United States Patent
Sha et al.

(10) Patent No.: US 10,196,407 B2
(45) Date of Patent: Feb. 5, 2019

(54) PROCESS FOR SILANE OLIGOMER COMPOSITION PREPARATION AND USE THEREOF

(71) Applicant: Wacker Chemie AG, Munich (DE)

(72) Inventors: Mark Sha, Shanghai (CN); Deng Ji, Shanghai (CN); Shuai (Tony) Tian, Wuxi (CN)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/517,177

(22) PCT Filed: Oct. 8, 2015

(86) PCT No.: PCT/EP2015/073311
§ 371 (c)(1),
(2) Date: Apr. 6, 2017

(87) PCT Pub. No.: WO2016/055595
PCT Pub. Date: Apr. 14, 2016

(65) Prior Publication Data
US 2017/0305940 A1   Oct. 26, 2017
US 2018/0127440 A9   May 10, 2018

(30) Foreign Application Priority Data

Oct. 9, 2014  (CN) .......................... 2014 1 0527479
Sep. 30, 2015  (CN) .......................... 2015 1 0638221

(51) Int. Cl.
  C07F 7/18    (2006.01)
  C08G 77/06   (2006.01)
  C08G 77/18   (2006.01)
  C08G 77/04   (2006.01)
  C08G 77/14   (2006.01)

(52) U.S. Cl.
  CPC ............ *C07F 7/188* (2013.01); *C07F 7/1804* (2013.01); *C08G 77/04* (2013.01); *C08G 77/06* (2013.01); *C08G 77/14* (2013.01); *C08G 77/18* (2013.01); *C08G 77/045* (2013.01)

(58) Field of Classification Search
  CPC ...... C08G 77/04; C08G 77/045; C08G 77/06; C08G 77/14
  See application file for complete search history.

(56) References Cited

U.S. PATENT DOCUMENTS

| | | | |
|---|---|---|---|
| 4,378,250 A | 3/1983 | Treadway et al. | |
| 6,069,259 A | 5/2000 | Crivello | |
| 7,632,909 B2 * | 12/2009 | Araki | C09J 183/04 528/12 |
| 8,394,972 B2 * | 3/2013 | Wassmer | C08G 77/14 549/215 |
| 2004/0099975 A1 | 5/2004 | Wu et al. | |
| 2006/0225612 A1 | 10/2006 | Lejeune et al. | |
| 2010/0191001 A1 | 7/2010 | Wassmer et al. | |
| 2011/0178238 A1 | 7/2011 | Koschabek et al. | |
| 2013/0137795 A1 | 5/2013 | Hara et al. | |

FOREIGN PATENT DOCUMENTS

| | | |
|---|---|---|
| CN | 101367939 B | 12/2012 |
| CN | 101367985 B | 4/2013 |
| CN | 101189281 B | 6/2013 |
| CN | 101365763 B | 9/2013 |
| EP | 0 072 473 A2 | 2/1983 |
| EP | 0 486 469 A1 | 5/1992 |
| JP | 2008537747 T2 | 9/2008 |
| WO | 2006/110331 A1 | 10/2006 |
| WO | 2009/021766 A1 | 2/2009 |
| WO | 2013096272 A1 | 6/2013 |

* cited by examiner

*Primary Examiner* — Marc S Zimmer
(74) *Attorney, Agent, or Firm* — Brooks Kushman P.C.

(57) ABSTRACT

Epoxy silane oligomers are prepared from a glycidoxypropyl alkoxysilane in the presence of an alcohol and an esterification and/or transesterification catalyst, and have improved storage stability. The oligomers are particularly useful as scrub-resistant additives for aqueous architectural coatings.

20 Claims, No Drawings

PROCESS FOR SILANE OLIGOMER COMPOSITION PREPARATION AND USE THEREOF

CROSS REFERENCE TO RELATED APPLICATIONS

This application is the U.S. National Phase of PCT Appln. No. PCT/EP2015/073311 filed Oct. 8, 2015, which claims priority to Chinese Application CN 201510638221.6, filed Sep. 30, 2015 and CN 201410527479.4, filed Oct. 9, 2014, the disclosures of which are incorporated in their entirety by reference herein.

BACKGROUND OF THE INVENTION

1. Field of the Invention

The present invention relates to a preparation method for silane oligomer compositions and their application in waterborne architectural coatings.

2. Description of the Related Art

The product CoatOSil MP 200 from Momentive is a relatively good silane oligomer composition in the present market. For details, see reference: Epoxy Silane Oligomer for Protective Coatings.

A method of preparing glycidoxypropylsilane oligomer compositions by using a solid catalyst is disclosed in patents CN101189281B and CN101365763B. The solid catalyst is selected from ion exchange resins, alkylammonium salts or the reaction products of quaternary ammonium organofunctional silanes with ceramic, silica gel, precipitated silica, alumina or aluminosilicate supports.

In WO2013096272A, a glycidoxypropylsilane oligomer composition is disclosed, which contains dimers, trimers, tetramers and other oligomers from the hydrolysis of glycidoxypropyldialkoxymethylsilane. The hydrolytic reactivity of this silane monomer is generally lower than silanes with trialkoxy functionality.

Patent CN101367939B discloses a method for controlled hydrolysis and condensation of epoxy functional silane under conditions employing boric acid, and no further hydrolysis or condensation catalyst is used apart from boric acid as the hydrolysis catalyst and condensation component.

Patent CN101367985B discloses a formulation which contains at least one oligosiloxane component and one hydroxyl-containing polymer component, wherein the oligosiloxane can be obtained through controlled hydrolysis and condensation of epoxy functional silane in the presence of boric acid.

U.S. Pat. No. 4,378,250 discloses a method of hydrolyzing glycidoxypropyltrimethoxysilane in 0.1N hydrochloric acid, wherein methanol is used as solvent, and the molar ratio of silane to water is 1:3.

SUMMARY OF THE INVENTION

The present invention provides a method for preparing glycidoxypropylsilane oligomer compositions with improved storage stability than comparable products in the present market by including an ester exchange or esterification reaction in the process. When these oligomers are added into waterborne architectural coating products, they can significantly improve the scrub resistance of the coatings.

DETAILED DESCRIPTION OF THE PREFERRED EMBODIMENTS

The invention thus pertains to a process for the preparation of an epoxy silane oligomer composition including an ester exchange reaction and/or an esterification reaction between an epoxy silane and a monovalent alcohol, and then a hydrolyzed condensation reaction of the products from the ester exchange reaction and/or the esterification reaction above, and obtaining an epoxy silane oligomer composition; or a hydrolyzed condensation reaction of an epoxy silane to obtain an epoxy silane oligomer composition, and then an ester exchange reaction and/or an esterification reaction between the epoxy silane oligomer composition and a monovalent alcohol.

The process described above, including the ester exchange reaction and/or the esterification reaction between a glycidoxypropyl functional silane having 2 or 3 alkoxy groups and a monovalent alcohol, followed by a controlled hydrolysis reaction of the products from the ester exchange reaction and/or the esterification reaction above, thus obtaining an epoxy silane oligomer composition; or a hydrolyzed condensation reaction of a glycidoxypropyl functional silane having 2 or 3 alkoxy groups, to obtain an epoxy silane oligomer composition, followed by an ester exchange reaction and/or an esterification reaction between the epoxy silane oligomer composition and a monovalent alcohol;

wherein the glycidoxypropyl functional silane having 2 or 3 alkoxy groups is selected from the group of 3-glycidoxypropyl trimethoxy silane, 3-glycidoxypropyl methyl dimethoxy silane, 3-glycidoxypropyl triethoxy silane, 3-glycidoxypropyl methyl diethoxy silane and mixtures thereof.

The process claimed above wherein monohydric alcohols are ROH, where R represents a $C_2$-$C_{12}$ alkyl radical, preferably being one or a mixture of several alcohols selected from ethanol, n-propanol, isopropanol, n-butanol and isobutanol, and more preferably being n-propanol, isopropanol, n-butanol or mixtures thereof.

In the process claimed above, "controlled hydrolysis" means that the molar ratio of water and glycidoxypropyl functional silane having 2 or 3 alkoxy groups is between 0.1 and 1.5, preferably 0.5-1.2.

The process claimed above which can be realized through the first embodiment comprises the following steps:

(a) mixing the glycidoxypropyl functional silane having 2 or 3 alkoxy groups, monovalent alcohol, catalyst for ester exchange reaction and/or esterification reaction and catalyst for hydrolysis and reacting under heating;

(b) adding water to the mixture obtained in step (a), and reacting by hydrolysis.

The process described above can also be realized through a second embodiment comprising the following steps:

(a) mixing the glycidoxypropyl functional silane having 2 or 3 alkoxy groups, monovalent alcohol, catalyst for ester exchange reaction and/or esterification reaction and reacting under heating;

(b) adding water and catalyst for hydrolysis successively or simultaneously to the mixture obtained in step (a) and reacting by hydrolyzing.

The process described above can also be realized through a third embodiment comprising the following steps:

(a) adding water and catalyst for hydrolysis successively or simultaneously to glycidoxypropyl functional silane having 2 or 3 alkoxy groups and hydrolyzing while heating;

(b) adding monovalent alcohol, catalyst for ester exchange reaction and/or an esterification reaction to the reaction mixture obtained in step (a) and reacting under heating.

In the process disclosed above, the catalyst for ester exchange reaction and/or an esterification reaction is preferably one or a mixture selected from the group containing acetic acid, glacial acetic acid, toluene sulfonic acid, sulfuric acid, hydrochloric acid, phosphoric acid, cation exchange resin; preferably acetic acid, glacial acetic acid; the catalyst for the hydrolysis reaction is one or a mixture selected from the group containing boric acid, metaboric acid, borate, $B_2O_3$, potassium fluoride, sodium fluoride, calcium fluoride, lithium fluoride, ionic exchange resin, titanate, organic tin catalyst; preferably boric acid, triethyl borate, tripropyl borate potassium fluoride, sodium fluoride or mixtures thereof.

In the first embodiment of the method above wherein when adding boric acid as hydrolysis catalyst in step (a), boric acid reacts with monohydric alcohol immediately producing borate ester, which serves as a hydrolysis catalyst in step (b); and if the monohydric alcohol used in step (a) is propanol, then tripropyl borate is produced.

In the process disclosed above, wherein after step (b) step (c) can be performed, the product obtained from step (b) is stirred for a period of time under 50-100° C., with a stirring time being 0.5-20 hr, preferably 1-10 hr, more preferably 1-6 hr.

In the process disclosed above, further comprise a step (d) to remove the byproduct alcohols to obtain the glycidoxypropyl functional silane oligomer, which can be performed in parallel with step (b) or step (c), preferable performed after step (b) or step (c).

In the process disclosed above, step (d) may be used to exclude low molecular weight substances from the product mixture through normal distillation under reduced pressure, or by short path evaporators or thin film evaporators, preferably through vacuum distillation for 0.5-5 hr at 50-80° C. and under 20-100 mbar in step (d), more preferably vacuum distillation for 0.5-7 hr at 50-70° C. and under 20-100 mbar, more preferably 2-7 hr.

In the process disclosed above, the molar ratio of monohydric alcohol to glycidoxypropyl functional silane containing 2 or 3 alkoxy groups is between 0.1 and 1.5, preferably 0.3-1.5.

In the process disclosed above, the molar ratio of catalyst for hydrolysis to glycidoxypropyl functional silane containing 2 or 3 alkoxy groups is between 0.001 and 0.6, preferably 0.001-0.009; and the mole ratio of catalyst forester exchange reaction and/or an esterification reaction and the glycidoxypropyl functional silane having 2 or 3 alkoxy groups is between 0.001-0.1, more preferably between 0.001-0.009.

In the process disclosed above, in step (b) water is evenly added over more than 30 minutes; preferably water is evenly added by at least 3 batches in more than 60 minutes; more preferably water is evenly added by at least 6 batches in more than 60 minutes; most preferably water is evenly added to the mixture obtained in step (a) with continuous dripping for more than 60 minutes.

A silane oligomer composition prepared through the method claimed above Is an epoxy silane oligomer composition, which is a mixture of epoxy silane oligomers with degrees of polymerization of 2-10, preferably with degrees of polymerization of 3-10, wherein more than 20 mole-%, preferably more the 40 mole-%, of all alkoxy groups in the oligomers are —OR' radicals, wherein R' is a $C_3$-$C_{12}$ alkyl radical, preferably an n-propyl radical, isopropyl radical, n-butyl radical or a mixture thereof.

In a epoxy silane oligomer composition according to the above, the oligomers are the silane condensation products with degrees of polymerization of 2-10, preferably with degrees of polymerization of 3-10.

An application of the silane oligomer compositions is their use as scrub resistant additives in water based architectural coatings.

The water based architectural coatings refer to coating systems that use water as main dispersing medium and are used to paint buildings, with preference to dispersions, in which carboxylic groups are predominant in the film-forming materials, including vinyl acetate-ethylene, acrylic, styrene-acrylic, silicone-acrylate, vinyl acetate-acrylate and vinyl tertcarbonate-acrylate dispersion systems.

3-glycidoxypropyltrimethoxysilane, under the trade name of GENIOSIL® GF80, can be obtained from Wacker Chemie AG 3-glycidoxypropyltriethoxysilane, under the trade name of GENIOSIL® GF82, can be obtained from Wacker Chemie AG Example 1

Add 25 g of anhydrous ethanol, 118 g of 3-glycidoxypropyltrimethoxy-silane into a 500 ml three-necked flask, and then add 2 g of boric acid and 0.2 g of 80% acetic acid while stirring, let them react for 60 min at 60-70° C.

Then divide 10.8 g of deionized water into six equal portions and add them in batches at intervals of 10 min. Next, let them react while stirring for another 4 hr at 60-70° C. At the same temperature, evaporate the free methanol, ethanol and borate by vacuum distillation for 2 hr. A colorless transparent liquid product is obtained.

Example 2

Add 25 g of anhydrous propanol, 118 g of 3-glycidoxypropyltrimethoxy-silane into a 500 ml three-necked flask, and then add 2 g of boric acid and 0.2 g of 80% acetic acid while stirring, let them react for 60 min at 60-70° C. Then divide 10.8 g of deionized water into six equal portions and add them in batches at intervals of 10 min. Next, let them react while stirring another 4 hr at 60-70° C. At the same temperature, evaporate the free methanol, propanol and borate by vacuum distillation for 2 hr. A colorless transparent liquid product is obtained.

Example 3

Add 25 g of anhydrous propanol, 118 g of 3-glycidoxypropyltrimethoxy-silane and 0.2 g of 80% acetic acid into a 500 ml three-necked flask, react at 70-75° C. for 60 mins; and then add 0.06 g potassium fluoride and 10.8 g of deionized water into the flask dropwise within 60 mins. Next, let them react while stirring another 2 hr at 50-60° C. Evaporate the free methanol, propanol by vacuum distillation at 70-75° C. for 5 hr. A light yellow transparent liquid product is obtained.

Example 4

Add 118 g of 3-glycidoxypropyltrimethoxysilane into a 500 ml three-necked flask, add 0.06 g potassium fluoride and 10.8 g of deionized water in to the flask dropwise in 60 mins. React at 50-60° C. for 2 hrs under stirring; vacuum distillation at 70-75° C. for 2 hr, methanol is evaporated. After filtration, the epoxy silane oligomer composition is obtained. Then add 25 g of anhydrous propanol, 0.55 g of 33% hydrochloric acid into the flask. Let them react while stirring for 60 mins at 70-75° C. Vacuum distillation at 70-75° C. for 2 hr is used to evaporate the free methanol, propanol. A light yellow transparent liquid product is obtained.

Comparative Example 1

Add 18 g of anhydrous ethanol, 118 g of 3-glycidoxy-propyltrimethoxy-silane into a 500 ml three-necked flask, heat to 60° C. while stirring.

Mix 2 g of boric acid, 0.2 g of 80% acetic acid and 9 g of deionized water and divide into six equal portions and add them in batches at intervals of 10 min.

Next, let them react while stirring for another 4 hr at 60-70° C. At the same temperature, evaporate the free methanol, ethanol and borate by vacuum distillation for 2 hr. A colorless transparent liquid product is obtained.

Comparative Example 2

Add 18 g of anhydrous ethanol, 118 g of 3-glycidoxy-propyltrimethoxy-silane into a 500 ml three-necked flask, heat to 60° C. while stirring.

Mix 1 g of boric acid, 0.2 g of 80% acetic acid and 18 g of deionized water and divide into six equal portions and add them in batches at intervals of 10 min.

Next, let them react while stirring for another 4 hr at 60-70° C. At the same temperature, evaporate the free methanol, ethanol and borate by vacuum distillation for 2 hr. A colorless transparent liquid product is obtained.

Comparative Example 3

Add 18 g of anhydrous ethanol, 139 g (0.5 mol) of 3-glycidoxypropyltriethoxysilane into a 500 ml three-necked flask, heat to 60° C. while stirring. Then add 2 g of boric acid and 0.2 g of 80% acetic acid while stirring, let them react for 60 min at 60-70° C. Then divide 10.8 g of deionized water into six equal portions and add them in batches at intervals of 10 min. Next, let them react while stirring for another 4 hr at 60-70° C. At the same temperature, evaporate the free ethanol and borate by vacuum distillation for 2 hr. A colorless transparent liquid product is obtained.

The formulations and property values of the silane oligomer compositions in examples and comparative examples are listed in Table 1.

TABLE 1

|  | Example 1 | Example 2 | Example 3 | Comparative Example 1 | Comparative Example 2 | Comparative Example 3 |
|---|---|---|---|---|---|---|
| Propanol (g) |  | 25 | 25 |  |  |  |
| Anhydrous ethanol (g) | 25 |  |  | 18 | 18 | 18 |
| 3-glycidoxypropyl trimethoxysilane (g) | 118 | 118 | 118 | 118 | 118 |  |
| 3-glycidoxypropyl triethoxysilane (g) |  |  |  |  |  | 139 |
| 80% acetic acid (g) | 0.2 | 0.2 | 0.2 | 0.2 | 0.2 | 0.2 |
| Boric acid (g) | 2 | 2 |  | 2 | 1 | 2 |
| Tributylborate (g) |  |  |  |  |  |  |
| potassium fluoride (g) |  |  | 0.06 |  |  |  |
| Water (g) | 10.8 | 10.8 | 10.8 | 9 | 18 | 10.8 |
| Product yield (g) | 108.7 | 122.7 | 110.2 | 105.3 | 105.9 | 138.8 |
| Viscosity (mPa.s) at 25° C. | 50.2 | 40.3 | 60.3 | 36.7 | 11,000 | 4.48 |
| Stability (30 days at RT) | Good | Good | Very Good | Good | Obviously thickening | Good |
| Non-volatile content % (105° C./3 h) | 74.15 | 67.31 | 93.7 | 78.06 | 84.5 |  |
| Epoxy content % | 6.46 | 6.15 | 6.35 | 5.78 |  | 6.33 |

In the viscosity stability indication, "Good" means the viscosity change within 30 days storage at room temperature is less than 100%; "Very Good" means the viscosity change within 30 days storage at room temperature is less than 10%; "Obviously thickening" means the viscosity change within 30 days storage at room temperature is much more than 1000.

In example 2, the product yield is obviously higher than that in example 1, indicating that the low molecular weight methoxy groups has been replaced by the high molecular weight propoxy groups. Furthermore, the viscosity of the product increases, indicating the production of mixed epoxy silane oligomer. The stability data of example 3 is much better than example 1 and 2, meaning that the reaction is more completed under catalyzed by fluorides, and the obtained epoxy silane oligomer is more stable. The viscosity of the product in comparative example 2 obviously increases after storage and the product is unstable during storage and application, indicating that when the molar ratio of water and glycidoxypropylalkyloxysilane equals to 2, the product is over-hydrolyzed, preventing the formation of ideal oligomer. Comparative example 3 uses 3-glycidoxypropyltri-ethoxysilane and ethanol as raw materials. The product yield is 138.8 g which is almost equal to the amount of raw materials used. Almost no transesterification occurs and the viscosity of the hydrolysates is very low, indicating that 3-glycidoxypropyltriethoxysilane monomers are of low activity and hydrolytic condensation of the monomers can hardly occur in a short period of time.

Application of Silane Oligomer Composition in Waterborne Architectural Coating:

The blank sample is a styrene-acrylic emulsion engineering paint ICI1000 from Akzo Nobel available in the market. Coating examples or coating comparative examples are obtained by adding 0.1 wt % (of total engineering paint amount) of silane oligomer composition, prepared through the method described in this invention or through the method described in a comparative method, into the blank sample and mixing uniformly (mixer 800 rpm for 10 min). Coating examples, coating comparative examples and blank sample are ensured to form coating films at the same time according to GB/T-9755-2001. The scrub resistance of group 1 is tested after drying for 7 days under standard conditions. The coating examples, coating comparative examples and blank samples are kept in a sealed condition at 50° C. for 14 days, and then removed. After cooling to room temperature, coating films are formed according to GB/T-9755-2001. The scrub resistance of group 2 is tested after drying for 7 days under standard conditions.

The composition of coating examples, coating comparative examples and blank sample are listed in Table 2.

TABLE 2

|  | Coating Example 1 | Coating Example 2 | Coating Example 3 | Coating Comparative Example 1 | Coating Comparative Example 2 | Blank sample |
|---|---|---|---|---|---|---|
| AkzoNobel engineering paint | 100 | 100 | 100 | 100 | 100 | 100 |
| Example 1 | 0.1 |  |  |  |  |  |
| Example 2 |  | 0.1 |  |  |  |  |
| Example 3 |  |  | 0.1 |  |  |  |
| Comparative Example 1 |  |  |  | 0.1 |  |  |
| Comparative Example 2 |  |  |  |  | 0.1 |  |

The cycle times of scrub resistance at room temperature and under accelerated aging conditions for coating examples, coating comparative examples and blank sample are listed in Table 3.

TABLE 3

|  | Coating Example 1 | Coating Example 2 | Coating Example 3 | Coating Comparative Example 1 | Coating Comparative Example 2 | Blank sample |
|---|---|---|---|---|---|---|
| Group 1 placed at room temperature | 3044 | 3265 | 3278 | 1256 | 1342 | 398 |
| Group 2 placed at 50° C. for 14 days | 435 | 460 | 468 | 250 | 377 | 199 |

According to the test, it is found that by adding a small amount of the silane oligomer composition prepared through the method described in this invention into waterborne architectural coating, the scrub resistance of the building coatings can obviously be improved. According to the test, it is found that the silane oligomer composition obtained in example 2 and 3 can most significantly improve the scrub resistance of the coatings, indicating the best hydrolytic stability of the silane oligomer composition containing high molecular weight propoxy groups. In the process of preparing comparative examples 1 and 2, a slight transesterification occurs along with hydrolytic condensation. Because of steric hindrance, the degree of transesterification of the comparative examples is lower than those in examples 1 and 2. The remaining methoxy groups are easily hydrolyzed in aqueous systems, causing obvious reduction in scrub resistance of the coatings after heat storage.

The invention claimed is:

1. A process for the preparation of an epoxy silane oligomer composition, comprising: reacting a glycidoxypropyl functional silane having 2 or 3 alkoxy groups and a monovalent alcohol in an ester exchange reaction and/or an esterification reaction, followed by a controlled hydrolysis reaction of the products from the ester exchange reaction and/or esterification reaction, obtaining an epoxy silane oligomer composition; or condensing by hydrolysis a glycidoxypropyl-functional silane having 2 or 3 alkoxy groups to obtain an epoxy silane oligomer composition, and then conducting an ester exchange reaction and/or an esterification reaction between the epoxy silane oligomer composition and a monovalent alcohol;

wherein the glycidoxypropyl functional silane having 2 or 3 alkoxy groups is selected from the group consisting of 3-glycidoxypropyltrimethoxysilane, 3-glycidoxypropylmethyldimethoxy silane, 3-glycidoxypropyltriethoxysilane, 3-glycidoxypropylmethyldiethoxysilane, and mixtures thereof, wherein the monovalent alcohol is selected from the group consisting of ethanol, n-propanol, isopropanol, n-butanol, isobutanol, and mixtures thereof, and wherein the alkyl group of the monovalent alcohols is/are different from the alkyl group of at least one alkoxy group of the glycidoxypropyl functional silane, and wherein the mole ratio of water to the 3-glycidoxypropyl-functional silane having 2 or 3 alkoxy groups is between 0.1-1.5.

2. The process of claim 1, wherein the mole ratio of water to the 3-glycidoxypropyl-functional silane is between 0.5-1.2.

3. The process of claim 1, comprising the following steps:
(a) mixing the glycidoxypropyl-functional silane having 2 or 3 alkoxy groups, monovalent alcohol, catalyst for ester exchange and/or esterification, and catalyst for hydrolysis, and reacting under heating; and
(b) adding water to the mixture obtained in step (a) and reacting by hydrolysis.

4. The process of claim 1, comprising the following steps:
(a) mixing the glycidoxypropyl-functional silane having 2 or 3 alkoxy groups, monovalent alcohol, catalyst for ester exchange and/or esterification and reacting under heating;
(b) adding water and catalyst for hydrolysis successively or simultaneously to the mixture obtained in step (a) and reacting by hydrolysis.

5. The process of claim 1, wherein the catalyst for ester exchange and/or an esterification is selected from the group consisting of acetic acid, glacial acetic acid, toluene sulfonic acid, sulfuric acid, hydrochloric acid, phosphoric acid, cation exchange resin and mixtures thereof; and the catalyst for hydrolysis is selected from the group consisting of boric acid, metaboric acid, borate, $B_2O_3$, potassium fluoride, sodium fluoride, calcium fluoride, lithium fluoride, ionic exchange resin, titanate, organic tin catalyst and mixtures thereof.

6. The process of claim 1, wherein the catalyst for ester exchange and/or an esterification is selected from the group consisting of acetic acid, glacial acetic acid and mixtures thereof; and the catalyst for hydrolysis is selected from the group consisting of boric acid, metaboric acid, borate, $B_2O_3$, potassium fluoride, sodium fluoride, calcium fluoride, lithium fluoride, ionic exchange resin, titanate, organic tin catalyst and mixtures thereof.

7. The process of claim 1, wherein the catalyst for ester exchange and/or an esterification is selected from the group consisting of acetic acid, glacial acetic acid, toluene sulfonic acid, sulfuric acid, hydrochloric acid, phosphoric acid, cation exchange resin and mixtures thereof; and the catalyst for hydrolysis is selected from the group consisting of boric acid, triethyl borate, tripropyl borate, potassium fluoride, sodium fluoride and mixtures thereof.

8. The process of claim 1, wherein the mole ratio of the monovalent alcohol and the glycidoxypropyl-functional silane having 2 or 3 alkoxy groups is between 0.1-1.5.

9. The process of claim 1, wherein the mole ratio of the monovalent alcohol and the glycidoxypropyl-functional silane having 2 or 3 alkoxy groups is between 0.3-1.5.

10. The process of claim 1, wherein the mole ratio of catalyst for hydrolysis and the glycidoxypropyl-functional silane having 2 or 3 alkoxy groups is between 0.001-0.6, and the mole ratio of catalyst for ester exchange and/or an esterification and the glycidoxypropyl-functional silane having 2 or 3 alkoxy groups is between 0.001-0.1.

11. An epoxy silane oligomer composition having at least two kinds of alkoxy groups, prepared by the process of claim 1.

12. The epoxy silane oligomer composition of claim 11, comprising epoxy silane oligomers with degrees of polymerization of 3-10, wherein more than 20 mole-%, of all alkoxy groups in the oligomers are —OR' radicals, wherein each R' individually is an n-propyl radical, isopropyl radical, or an n-butyl radical, and the remaining alkoxy groups are methoxy and/or ethoxy groups.

13. The epoxy silane oligomer composition of claim 11, comprising epoxy silane oligomers with degrees of polymerization of 3-10, wherein more than 40 mole-%, of all alkoxy groups in the oligomers are —OR' radicals, wherein each R' individually is an n-propyl radical, isopropyl radical, or an n-butyl radical, and the remaining alkoxy groups are methoxy and/or ethoxy groups.

14. In a water based architectural coating, the improvement comprising increasing scrub resistance of the coating by adding to the water based architectural coating, a silane oligomer composition of claim 11.

15. A process for the preparation of an epoxy silane oligomer composition, comprising: reacting a glycidoxypropyl functional silane having 2 or 3 alkoxy groups and a monovalent alcohol in an ester exchange reaction and/or an esterification reaction, followed by a controlled hydrolysis reaction of the products from the ester exchange reaction and/or esterification reaction, obtaining an epoxy silane oligomer composition;
wherein the glycidoxypropyl functional silane having 2 or 3 alkoxy groups is selected from the group consisting of 3-glycidoxypropyltrimethoxysilane, 3-glycidoxypropylmethyldimethoxy silane, 3-glycidoxypropyltriethoxysilane, 3-glycidoxypropylmethyldiethoxysilane, and mixtures thereof, wherein the monovalent alcohol is selected from the group consisting of ethanol, n-propanol, isopropanol, n-butanol, isobutanol, and mixtures thereof, and wherein the alkyl group of the monovalent alcohols is/are different from the alkyl group of at least one alkoxy group of the glycidoxypropyl functional silane,
and wherein the mole ratio of water to the 3-glycidoxypropyl-functional silane having 2 or 3 alkoxy groups is between 0.1-1.5.

16. The process of claim 15, wherein the mole ratio of water to the 3-glycidoxypropyl-functional silane is between 0.5-1.2.

17. The process of claim 15, comprising the following steps:
(a) mixing the glycidoxypropyl-functional silane having 2 or 3 alkoxy groups, monovalent alcohol, catalyst for ester exchange and/or esterification, and catalyst for hydrolysis, and reacting under heating; and
(b) adding water to the mixture obtained in step (a) and reacting by hydrolysis.

18. The process of claim 15, comprising the following steps:
(a) mixing the glycidoxypropyl-functional silane having 2 or 3 alkoxy groups, monovalent alcohol, catalyst for ester exchange and/or esterification and reacting under heating;
(b) adding water and catalyst for hydrolysis successively or simultaneously to the mixture obtained in step (a) and reacting by hydrolysis.

19. The process of claim 15, wherein the mole ratio of the monovalent alcohol and the glycidoxypropyl-functional silane having 2 or 3 alkoxy groups is between 0.1-1.5.

20. The epoxy silane oligomer composition of claim 11, comprising epoxy silane oligomers with degrees of polymerization of 3-10, wherein more than 20 mole-%, of all alkoxy groups in the oligomers are —OR' radicals, wherein each R' individually is an n-propyl radical, isopropyl radical, or an n-butyl radical, and the remaining alkoxy groups are methoxy and/or ethoxy groups.

* * * * *